United States Patent
Kall et al.

(10) Patent No.: US 11,076,932 B2
(45) Date of Patent: Aug. 3, 2021

(54) WIRELESS SENSOR AND MONITORED PATIENT ASSOCIATION SYSTEM AND METHOD

(71) Applicant: General Electric Company, Schenectady, NY (US)

(72) Inventors: Magnus Kall, Helsinki (FI); Tuomas Laine, Helsinki (FI); Mika Tapaninaho, Helsinki (FI); Sakari Lamminmaki, Helsinki (FI)

(73) Assignee: General Electric Company, Schenectady, NY (US)

( * ) Notice: Subject to any disclaimer, the term of this patent is extended or adjusted under 35 U.S.C. 154(b) by 886 days.

(21) Appl. No.: 15/365,196

(22) Filed: Nov. 30, 2016

(65) Prior Publication Data
US 2018/0147024 A1    May 31, 2018

(51) Int. Cl.
*A61B 90/98*     (2016.01)
*G16H 10/60*     (2018.01)
(Continued)

(52) U.S. Cl.
CPC .............. *A61B 90/98* (2016.02); *A61B 5/002* (2013.01); *A61B 5/0015* (2013.01); *A61B 5/0031* (2013.01); *A61B 5/053* (2013.01); *A61B 5/1172* (2013.01); *A61B 5/1473* (2013.01); *A61B 5/14517* (2013.01); *A61B 5/14546* (2013.01); *A61M 5/14276* (2013.01); *A61N 1/37217* (2013.01); *G16H 10/60* (2018.01); *G16H 40/63* (2018.01); *G16H 40/67* (2018.01); *A61B 5/117* (2013.01); *A61B 2562/08* (2013.01); *A61M 2205/3523* (2013.01); *A61M 2205/609* (2013.01)

(58) Field of Classification Search
CPC ........... A61B 90/98; A61B 5/00; A61B 5/053; A61B 5/1172; A61B 5/145; A61B 5/1473; A61B 5/14517; A61B 5/0031; A61B 5/002; A61B 5/14546; A61B 5/0015; A61B 5/117; A61B 2562/08; A61M 5/142; A61M 5/14276; A61M 2205/609; A61M 2205/3523; A61N 1/372; A61N 1/37217; G16H 10/60; G16H 40/63; G16H 40/67
See application file for complete search history.

(56) References Cited

U.S. PATENT DOCUMENTS 9,220,463 B2    12/2015  Grubis
9,443,059 B2    9/2016   Grubis
(Continued)

OTHER PUBLICATIONS

International Search Report and Written Opinion for International Application No. PCT/US2017/061982, dated Mar. 1, 2018. 11 pages.

*Primary Examiner* — Eric J Messersmith
(74) *Attorney, Agent, or Firm* — Andrus Intellectual Property Law, LLP

(57) ABSTRACT

Systems and methods for wireless sensing include a wireless senor which includes a physiological sensor and an identification sensor. The physiological sensor obtains physiological data from a patient and the identification sensor detects a unique characteristic of the patient as identification data. The identification data is used to produce a unique identifier which is transmitted wirelessly from the wireless sensor along with the physiological data to associate the transmitted physiological data to the patient.

20 Claims, 3 Drawing Sheets

(51) Int. Cl.
*A61B 5/00* (2006.01)
*G16H 40/67* (2018.01)
*G16H 40/63* (2018.01)
*A61B 5/053* (2021.01)
*A61B 5/1172* (2016.01)
*A61B 5/145* (2006.01)
*A61B 5/1473* (2006.01)
*A61M 5/142* (2006.01)
*A61N 1/372* (2006.01)
*A61B 5/117* (2016.01)

(56) References Cited

U.S. PATENT DOCUMENTS

| | | | |
|---|---|---|---|
| 2009/0043180 | A1 | 2/2009 | Tschautscher |
| 2010/0328320 | A1* | 12/2010 | Kerstna ............... G06Q 50/24 345/501 |
| 2012/0158428 | A1* | 6/2012 | Nuthi ............... G16H 20/30 705/3 |
| 2013/0106568 | A1* | 5/2013 | Harrold ............... A61B 5/1172 340/3.1 |
| 2015/0028996 | A1* | 1/2015 | Agrafioti ............... G06F 21/34 340/5.82 |
| 2015/0317855 | A1* | 11/2015 | Sezan ............... A61B 5/1171 340/5.52 |
| 2016/0058350 | A1* | 3/2016 | Medina ............... A61B 5/14551 600/324 |
| 2016/0183812 | A1* | 6/2016 | Zhang ............... A61B 5/117 600/301 |
| 2016/0338891 | A1* | 11/2016 | Agdeppa ............... A61B 5/113 |
| 2016/0342782 | A1* | 11/2016 | Mullins ............... G06F 21/32 |
| 2017/0124256 | A1* | 5/2017 | Nantz ............... G16H 40/67 |
| 2018/0199824 | A1* | 7/2018 | Centen ............... A61B 5/7203 |

* cited by examiner

WIRELESS SENSOR AND MONITORED PATIENT ASSOCIATION SYSTEM AND METHOD

BACKGROUND

The present disclosure is related to the field of wireless sensing. More specifically, the present disclosure is related to evaluating an association between a wireless sensor and a monitored patient.

Monitoring vital signs is an important part of patient care as the general or particular health of the patient is determined, in part, through measurement and interpretation of key physiological indicators. Well-known parameters of patient health include blood pressure, oxygen saturation ($SpO_2$), and features of the electrocardiogram (ECG). However, the utilization of physiological instrumentation to obtain these measurements at the bed side of a patient also possess well-known burdens to the clinical environment. The presence of cables, catheters, and tubing connecting the patient and sensors to the instrumentation configured to provide all monitoring or therapeutic care can diminish productivity and the quality of patient care. For example, rotating a patient to alleviate bed sores or ambulating about the room can be problematic if one is saddled with tethered devices. Procedural delays stemming from cable management also contribute to a great percentage of time dedicated to routine, mundane tasks not directly related to treatment of the patient's illness.

Wireless communication technology leveraged to patient monitoring may at least mitigate some of the problems associated with cable clutter and device management. With instrumentation becoming wireless, the management of such devices is eased. In addition, wireless instrumentation/devices greatly reduce the burden associated with cable management.

Wireless patient monitoring networks, however, bring new problems that need to be addressed for proper implementation of a wireless monitoring regime. In many instances, whether using a wireless monitoring system or a wired system, elements of the system communicate with at least one central management device. In the hospital environment, this management device is often used to relay monitored information to an infrastructure that allows health care professionals to analyze the monitored information from an outside location (e.g. a nurse station). In other wireless systems, the management device may be integrated with a central processing unit that analyzes the incoming device information. When cables are removed from these devices, a user of the system can no longer safe guard that the devices are properly connected to the patient to be monitored by the management device by simply ensuring that the cables extend from the management device to the correct patient. That is, without cables, a health care provider or other operator lacks the visual cues associated with cables to assure that the sensing devices are properly connected to the proper patient to be monitored by the management device. Alternatively, as wireless sensing systems proliferate in a care setting, wireless sensing devices may inadvertently become communicatively connected with a management device associated with another patient. Again, without the visual cues of the cable, a healthcare provider or other operator lacks a tool for fast and accurate confirmation that the management device is receiving physiological data from a specified patient and that patient only.

U.S. Pat. No. 9,443,059 discloses systems and methods of evaluating an association between a wireless sensor and a monitored patient including a plurality of wireless sensors each having a wireless communication system and a sensor. A processor receives measured physiological parameter data from the wireless sensors and establishes an association status between each of the wireless sensors and the monitored patient based upon identified characteristics in the physiological parameter data.

BRIEF DISCLOSURE

An exemplary embodiment of a sensor includes a physiological sensor which is configured to obtain physiological data from a patient. An identification sensor is configured to detect a unique characteristic of the patient as identification data. A processor receives the physiological data and the identification data. The processor produces a unique identifier from the identification data. A communication system is operable by the processor to wirelessly transmit the physiological data and the unique identifier.

An exemplary embodiment of a wireless sensing system includes a first wireless sensor and a second wireless sensor. The first wireless sensor includes a physiological sensor configured to obtain first physiological data from a first patient and an identification sensor configured to detect a unique characteristic of the first patient to obtain further identification data. The first wireless sensor includes a processor that receives the first physiological data and the first identification data. The processor produces a first unique identifier from the first identification data. The wireless sensing system includes a communication system operated by the processor to wirelessly transmit the first physiological and the first unique identifier. The second wireless sensor includes a physiological sensor configured to obtain second physiological data from a second patient and an identification sensor configured to detect a unique characteristic of the second patient to obtain second identification data. A processor receives the second physiological data and the second identification data and produces a second unique identifier fro the second identification data. The processor operates a communication system to wirelessly transmit the second physiological data and the second unique identifier. A hub is configured to define a communication area within which a communication system of the hub will receive transmission from communication systems of wireless sensors within the communication area. A processor is communicatively connected to the hub. The processor receives the first physiological data and first unique identifier from the first wireless sensor and second physiological data and the second unique identifier from the second wireless sensor.

An exemplary embodiment of a method of wireless sensing includes placing a first plurality of wireless sensors on a first patient. Each wireless sensor of the first plurality of wireless sensors individually produces the same first unique identifier based upon a characteristic of a first patient. Each wireless sensor of the first plurality of wireless sensors obtain physiological data from the first patient. Each wireless sensor of the first plurality of wireless sensors transmits the obtained physiological data and the first unique identifier. The physiological data and the first unique identifier are received at a processor from the first plurality of wireless sensors. The received physiological data is associated to the first patient based upon the received first unique identifier.

A further exemplary embodiment of a wireless sensing system includes a first wireless sensor. The first wireless sensor includes a physiological sensor configured to obtain first physiological data from a first patient. The first wireless sensor includes an identification sensor configured to detect a unique characteristic of the first patient to obtain first identification data. The first wireless sensor further includes a first sensor processor that receives the first physiological data and the first identification data and operates a communication system to wirelessly transmit the first physiological data and the first identification data. The wireless sensing system includes a second wireless sensor which includes a physiological sensor configured to obtain second physiological data from a second patient. The second wireless sensor includes an identification sensor configured to detect a unique characteristic of the second patient to obtain second identification data. The second wireless sensor further includes a second sensor processor that receives the second physiological data and the second identification data and operates a communication system to wirelessly transmit the second physiological data and the second identification data. A communication system defines a communication area within which the communication system defining the communication area will receive transmissions from wireless sensors within the communication area. A processor is communicatively connected to the communication system. The processor receives the first physiological data, the first identification data, second physiological data, second identification data from the communication system. The processor produces a first unique identifier from the first identification data and produces a second unique identifier from the second identification data. The processor stores the first physiological data in association with the first unique identifier and stores the second physiological data in association with the second unique identifier.

DETAILED DISCLOSURE

Figure 1:
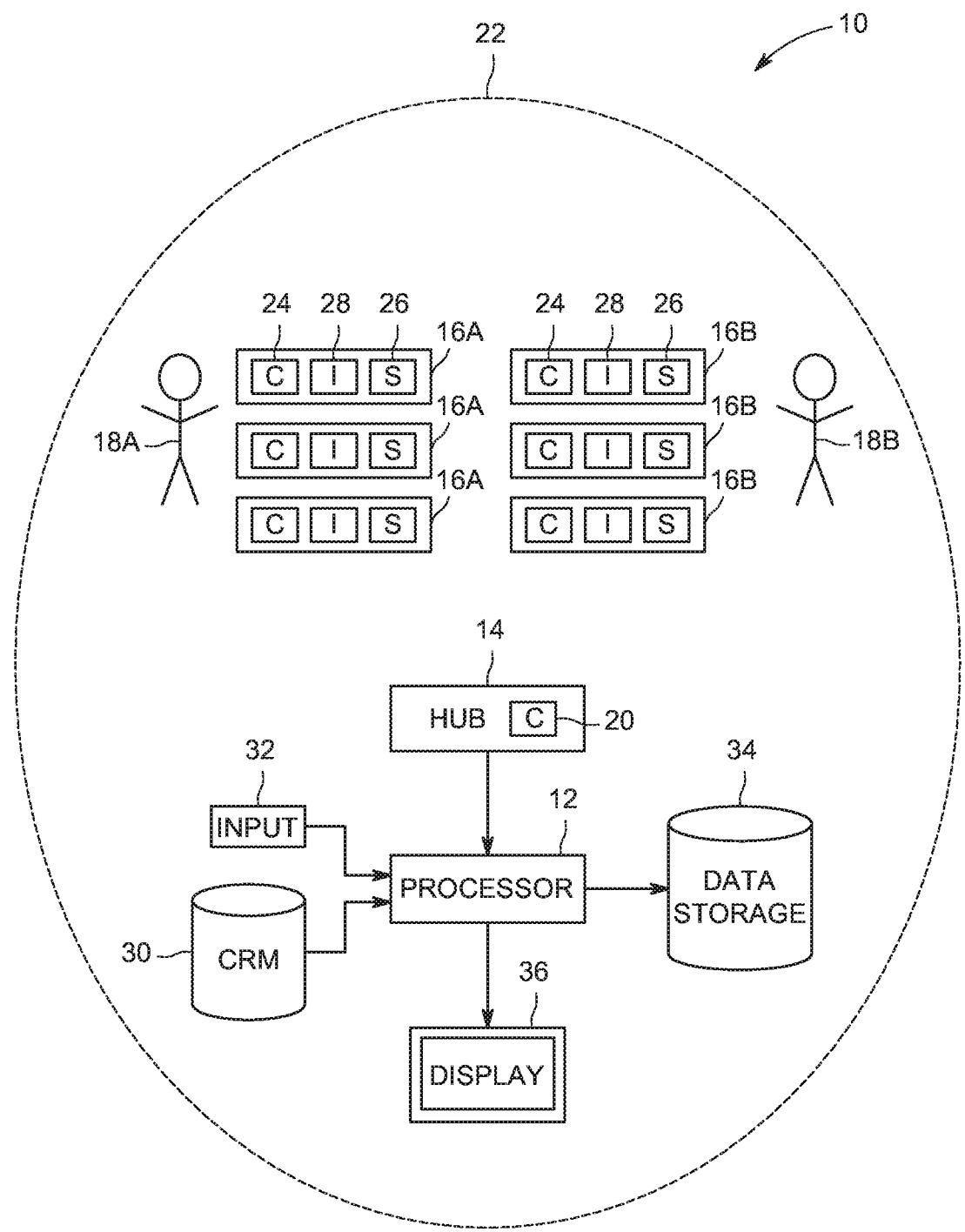
FIG. 1 is a schematic diagram of an exemplary embodiment of a wireless system.

FIG. 1 is a schematic diagram of a wireless system 10. The wireless system 10 includes a processor 12 that is configured in the manner as disclosed herein to receive a plurality of signals acquired by the wireless system 10 and evaluate the signals. The wireless system 10 further includes a hub 14 that is configured to communicate both with the processor 12 and with a plurality of wireless sensors 16 configured to be secured to a patient 18. It will be understood that in embodiments, the hub 14 may be an independent device that is communicatively connected to the processor 12, while in other embodiments the hub 14 may be integrated into a single device with the processor 12. In still further embodiments, the hub 14 may be a wearable device removably secured to a patient, while in other embodiments, the hub 14 may be one of many distributed throughout a care facility.

It will be recognized that in some embodiments, the processor 12 may be local to the hub 14 and/or the wireless system 10 generally. However, in other embodiments, the processor 12 may be remotely located across a communication network from the hub 14, for example in a cloud-based computing arrangement. In still further embodiments, the functionalities as described herein attributable to the processor 12 may exemplarily be performed by multiple processors, for example in a distributed processing arrangement. The processor 12 may exemplarily operate in a similar manner as described herein under any of these arrangements and any such implementations are considered to be within the scope of the processor of the present disclosure. In other exemplary embodiments, wherein the hub 14 is integrated with the processor 12, the wireless sensors 16 may communicate directly with the processor 12 through a long range wireless network, for example, a WLAN or WMTS communication network.

The hub 14 includes a wireless communication system 20 that exemplarily creates a communication area or range 22 within which the hub 14 may be communicatively connected with one or more of the wireless sensors 16. The wireless sensors 16 further each include a wireless communication system 24. It will be understood that the wireless communication systems 20, 24 respectively of the hub 14 and the wireless sensors 16 will be communicatively compatible. In an exemplary embodiment, the wireless communication systems 20, 24 are radio frequency (RF) wireless communication devices. However, it will be understood that in alternative embodiments, the wireless communication systems 20, 24 may include optical, magnetic, ultrasound, visible light, infrared, or other forms of wireless communication systems.

While embodiments of the wireless sensors 16 may include other components as described in further detail herein, each of the wireless sensors 16 include at least one physiological sensor 26 and at least one patient identification sensor 28. The physiological sensor 26 is operable to acquire or measure at least one physiological parameter or signal. In the present disclosure, the exemplary embodiment and application of a health care setting is used for descriptive purposes, although, it will be recognized that alternative embodiments of the systems and methods as disclosed herein may be used in conjunction with other applications in which a plurality of personal wireless sensors must be managed. Thus, in the exemplary embodiment given herein, the physiological sensors 26 may be physiological sensors that are configured to acquire physiological data from a patient 18. In non-limiting embodiments, the physiological sensors 24 may include heart rate, pulse rate, temperature, electrocardiogram (ECG), blood pressure (e.g. NIBP), respiration, physical movement, electroencephalogram (EEG) and others as may be recognized by a person of ordinary skill in the art.

In embodiments, the sensors of the wireless sensors measure or otherwise acquire at least one physiological signal from the patient 18 and process the physiological signal as physiological data. The physiological data may be a digitized physiological signal or may be physiological data derived from a physiological signal obtained by the physiological sensor 26. For example, in the exemplary case of ECG, the physiological data may be a digitized ECG waveform or may be an instantaneous pulse rate derived from the ECG waveform. The wireless communication systems 24 of the wireless sensors 16 work with the wireless communication system 20 of the hub 14 to wirelessly transmit the acquired physiological data through the hub 14 to the processor 12.

The patient identification sensor 28 operates as described in further detail herein to sense a characteristic of the patient that can be used by the system as disclosed herein to uniquely identify the patient. The characteristic of the patient may exemplarily be a signal internal to the patient, a physical property or a chemical property. This unique identification of the patient can be appended to the physiological data transmitted by the wireless communication system 24 to the hub 14 so that the processor 12 receiving physiological data from a plurality of patients can correctly associate the physiological data to the appropriate patient. In non-limiting embodiments, the patient identification sensors 28 may detect a unique chemical composition, protein or protein signature, or genes or DNA of the patient. In other exemplary embodiments, the patient identification sensor 28 may use a unique quality or characteristic of a patient's biopotentials, including but not limited to ECG, EMG, or EEG, such unique quality or characteristic may be used as a biopotential fingerprint for the patient. In still further exemplary embodiments, the patient identification sensor 28 may detect a potential or other signal emitted from a device internal to the patient. Exemplary embodiments of such implantable devices include a pacemaker, an insulin pump, or an identification device. Such implantable devices would be pre-existing to the patient and may already emit or be able to emit a unique identifying signal.

As depicted in FIG. 1, the wireless system 10 is particularly applicable for distinguishing the transmissions of wireless sensors 16 associated with particular patients 18 when multiple patients 18A, 18B with wireless sensors 16A, 16B are proximally located to one another, and particularly proximally located to a single hub 14, such that the hub 14 is concurrently receiving wireless transmissions from wireless sensors 16A, 16B associated with multiple patients 18A, 18B. Similarly, this is applicable with ambulatory patients who may move about a medical care facility and thus at any given time the wireless transmissions from the wireless sensors 16 associated with patients 18 may be received by one or more hubs 14 of a plurality of hubs 14 distributed throughout the medical care facility. As described in further detail herein, embodiments of the wireless system 10, intrinsically produce a unique identifier for each patient and append the unique identifier to the transmissions of physiological data so that the physiological data can be sorted to the appropriate patients by the processor 12 after receiving the transmitted physiological data from multiple patients.

Currently available wireless monitoring solutions require a manual or partially automated registration process to associate each wireless sensor to a particular patient. This may exemplarily be currently performed using Bluetooth pairing with pin codes, near-field communication (NFC) pairing, or WiFi direct printers. This registration process is performed with manual interaction by a clinician with both the wireless sensors and the monitoring system to create an association between a signal of each wireless sensor and the patient to be monitored by that sensor. This manual registration process offers opportunities for each wireless sensor to be incorrectly registered, and further uses a different association between each sensor and the patient to be monitored. Embodiments as disclosed herein use a unique aspect of the patient which is either transduced by the physiological sensor or a separate identification sensor to instead provide the association between the physiological data sensed by the wireless sensor and the patient record in the monitoring system. By using a identifying property intrinsic to the patient, registration of individual wireless sensors can be made more reliable, or eliminated altogether.

In exemplary embodiments, the wireless signals transmitted from each of the wireless sensors 16 are appended with identification data based upon the unique quality or characteristic detected from the patient by the identification sensor. As described in further detail herein, the wireless sensor 16 uses the unique quality or characteristic detected from the patient to create identification data that is unique to the patient and can be used by the processor 12 to sort the wireless signals obtained by the hub 14 between the various patients 16A, 16B being wirelessly monitored.

The processor 12 is connected to at least one computer readable medium 30. In embodiments, the processor 12 executes computer readable code stored on the computer readable medium 30 as software and firmware. The execution of the computer readable code causes the processor 12 to operate in a manner such as to carry out the operations and functions as described herein. In an exemplary embodiment, the computer readable medium 30 is an integral part of the processor 12.

An input device 32 is further connected to the processor 12 whereby a technician can enter information including information regarding the patient to be monitored, the wireless sensors used, and/or the physiological condition of the patient. While many embodiments, as described herein, can eliminate the need to individually register wireless sensors 16 to a particular patient, in some embodiments, the unique identification produced by the wireless sensor may be used to further register wireless sensors to a particular patient.

In other embodiments, once the unique identifier is known by the wireless monitoring system, no registration is needed, as the unique identifier as provided by each wireless sensor may be used to sort the received signals from all of the wireless sensors upon receipt by the system. In some embodiments as disclosed herein, the input device 32 may be used by the clinician or technician to create the initial association between the patient's unique identification and the patient record within the wireless monitoring system. In exemplary embodiments, this association may include the identification and input of the unique identification of the patient to the system. The unique identification may exemplarily be a DNA sequence, protein signature, or other unique chemical or bio-chemical identifier of the patient. In still further exemplary embodiments, the unique identifier may be a signal propagated through the patient, for example from another device implanted within the patient. In exemplary embodiments, the unique identifier may be determined by a wireless sensor 16 of the system and transmitted in addition to the transmission of the physiological data, while in other embodiments, the unique identifier may be produced, exemplarily by the processor 12, after receiving the identification data from a sensor. The unique identifier may be input into the system through the input device 32 or may be previously stored within a patient file, exemplarily a patient electronic medical record (EMR), stored in data storage 34 which is communicatively connected to the processor 12.

The processor 12 is communicatively connected to the data storage 34, for example by a wired or wireless communication system. The data storage 34 may be located on a computer readable medium that is either local to or remote from the processor 12. In a non-limiting embodiment, the data storage 34 may be implemented in a cloud-based computing system that operates to manage the patient information, exemplarily in the EMR. Thus, the data storage 34 may be communicatively connected to the processor 12 through a local hospital intranet or a wide area network exemplarily over the Internet. In one embodiment, both the acquired physiological data received from the plurality of wireless sensors and the unique identifiers of the patients are stored in the data storage 34.

The processor 12 further operates a graphical display 36 that may be operated by the processor 12 to visually present the physiological data obtained by the system. In embodiments, the processor 12 may operate the graphical display 36 to additionally visually present indications of the wireless sensors from which the processor is receiving transmissions of physiological data and the patients to which each of the wireless sensors are associated. It will be recognized that the system as disclosed herein may be used in conjunction with other systems and methods for the association and identification of wireless sensors to patients. Thus, in such embodiments, the graphical display 36 may be further operated to present indications of lost wireless sensors, lost wireless sensor signals, or wireless sensor signals whose association with a patient has reduced confidence or is called into question. The graphical display 36 operates to present such information in a graphical user interface (GUI) which may be configured in a variety of manners to visually convey this information. In embodiments, the graphical display 36 may be a flat panel display or may be a display associated with a laptop or tablet computer, or a display of a mobile device. In still further embodiments, the display 36 may have touch sensitive capabilities and as such operate as both the display 36 as well as the input device 32. In still further embodiments, the display 36 may further be operated by the processor 12 to present some or all of the physiological data acquired from the monitored patient by the plurality of wireless sensors 16.

Figure 2:
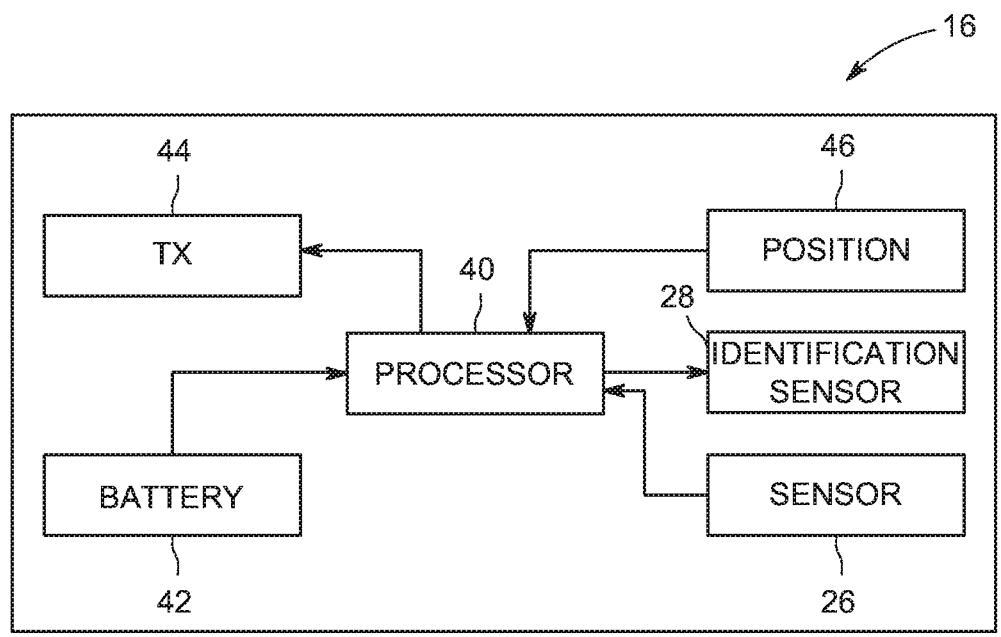
FIG. 2 is a schematic diagram of an exemplary embodiment of a wireless sensor.

FIG. 2 depicts a more detailed exemplary embodiment of a wireless sensor 16 such as may be used in conjunction with the wireless system 10 depicted in FIG. 1. The wireless sensor 16 includes a processor 40 that executes software or firmware stored at the processor 40 in order to carry out the functions as described in further detail herein. The wireless sensor 16 further includes a battery 42 that provides power to the processor 40 and other components of the wireless sensor requiring energization, either directly or indirectly from the battery 42. In an embodiment, the wireless sensor 16 may be constructed such that the battery 42 is replaceable or rechargeable. In such embodiments, the wireless sensor 16 may be configured to be reused and the battery 42 replaced or recharged in order to extend the life of the wireless sensor. In other embodiments, the wireless sensor 16 may be disposable after the power is drained from the battery 42.

As described above, the wireless sensor 16 is configured to be secured to the patient to be monitored and to wirelessly transmit patient data through an interaction between a wireless communication system 20 of a hub 14, with a wireless communication system 24 of the wireless sensor 16. In an exemplary embodiment, the communication system 24 of the wireless sensor 16 includes a transmitter 44 in order to broadcast or otherwise transmit the physiological data from the wireless sensor 16. The transmitter 44 may include any of a variety of known communication transmitters, including, but not limited to radio frequency, infrared, visible light, or ultrasonic, or other known transmission implementations.

The wireless sensor 16 includes the physiological sensor 26 communicatively connected to the processor 40. The physiological sensor 26 is configured to acquire or otherwise measure a physiological parameter from the patient. Non-limiting examples of physiological parameters that may be measured or acquired, include biopotentials such as electrocardiogram (ECG), electromyogram (EMG), and electroencephalogram (EEG). The sensor 26 may also be configured to acquire other physiological parameters such a heart rate, oxygen saturation ($SPO_2$), blood pressure, such as acquired by noninvasive blood pressure (NIBP) monitoring, respiration rate, motion detection, or temperature. However, these are merely exemplary of the types of sensors that may be incorporated into the wireless sensor 16 and are not intended to be limiting.

The wireless sensor 16 further includes the patient identification sensor 28. As described above, the patient identification sensor 28 operates to detect a unique characteristic of the patient. The patient identification sensor measures or otherwise obtains identification data as will be described in further detail herein. The identification data is provided to the processor 40 which creates a unique identifier based upon the identification data. This unique identifier based upon a characteristic of the patient is used to register the wireless sensor 16 to that particular patient. As patients ambulate around the medical care facility, the physiological data transmitted by the wireless sensors 16 of multiple patients 18A, 18B may be detected by a single hub 14 the physiological data transmitted by the wireless sensors of a single patient 18 may be detected by multiple hubs. The processor 40 operates the transmitter 44 to transmit the physiological data and the unique identifier. In an embodiment, the unique identifier is appended to the physiological data, while in another embodiment, the unique identifier is transmitted in association or conjunction with the physiological data. The unique identifier transmitted with the physiological data from the wireless sensor 16 is self-identifying of the association between the wireless sensor 16 and the patient being monitored. The unique identifier can be used by the processor 20 of the system 10 to sort the plurality of physiological data transmissions to the appropriate patients.

As previously noted, in an alternative embodiment, the processor 40 operates the transmitter 44 to transmit the identification data in addition to the physiological data. This embodiment may exemplarily be used in the event that the processing of the identification data to produce the unique identifier is particularly complex or could be beneficially processed by another processor rather than the processor 40 of the wireless sensor 16. In an embodiment, this may occur if producing the unique identifier takes more computing power than is economically viable for the processor 40. In non-limiting embodiments, artificial intelligence, DNA or other biological sequencing, or computationally intensive signal processing of biopotentials are some examples of identification data that may be advantageously analyzed remotely from the processor 40 of the wireless sensor 16.

In an exemplary embodiment, the patient identification sensor 28 is a chemical or biochemical sensor. The chemical or biochemical sensor analyzes a substance at the surface of the sensor. Non-limiting examples of substances include tissue, for example skin, or perspiration. A still further embodiment may make a microabrasion on the patient's skin either to sample skin or to break the skin to sample blood or another tissue of the patient. The chemical or biochemical sensor analyzes the sample to identify a unique chemical or biochemical signature of the patient. In one example, the signature may be the presence of one or more proteins in the sample. In another example, the signature may be one or more genes identified in the patient's DNA.

In other exemplary embodiments, the patient identification sensor 28 may use a unique characteristic of a patient's biopotentials, including but not limited to ECG, EMG, or EEG, such unique characteristic may be used as a biopotential fingerprint for the patient. In a non-limiting embodiment, this may be an EEG based brain fingerprint. In still further exemplary embodiments, the patient identification sensor 28 may detect a potential or other signal emitted from a device internal to the patient. Exemplary embodiments of such implantable devices include a pacemaker, an insulin pump, or an identification device. Such implantable devices would be pre-existing to the patient and may already emit or be able to emit a unique identifying signal. It will be recognized that in some exemplary embodiments wherein the unique quality or characteristic is a potential or biopotential, the patient identification sensor 28 may be embodied in the same sensor as a physiological sensor configured to obtain a biopotential. In such embodiments, although the sensor obtains the same raw potential signal for both purposes, the processor 40 may process the raw potential signal differently to identify both the physiological data of the biopotential as well as to detect the potential or signal used to create the identification data.

Embodiments of the wireless sensor 38 may further include a position detector 46. In an exemplary embodiment, the position detector 46 may be a global positioning system (GPS) detector or other TRLS (Real Time Location Service). The position detector 46 further provides the location of the wireless sensor 38 and can be transmitted by the transmitter 44 along with the physiological data collected by the sensor 26.

Figure 3:
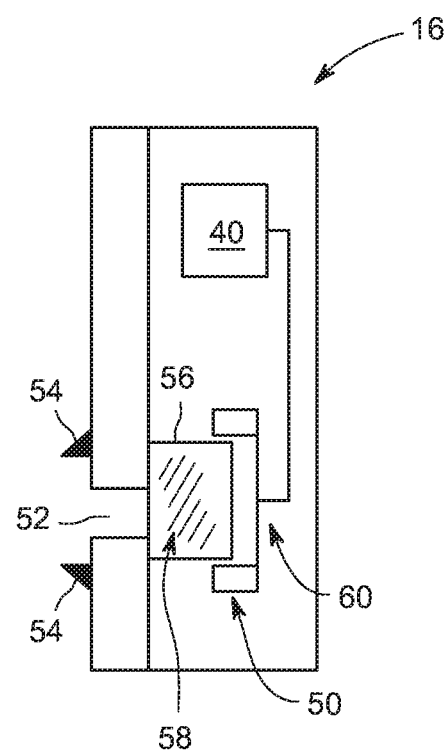
FIG. 3 depicts an exemplary embodiment of a patient identification sensor.

FIG. 3 depicts a wireless sensor 16 with an exemplary embodiment of patient identification sensor 50 configured as a chemical or biochemical sensor. In a non-limiting embodiment, the patient identification sensor is a microfluidic device. In the embodiment depicted, a capillary sample tube 52 draws a fluid sample (e.g. perspiration) into the sensor 50. In another embodiment, the patient identification sensor includes one or more projections 54, which may exemplarily be micro-abraders to break or loose skin cells or substances from the skin. In another embodiment, the one or more projections 54 are sharp and configured to break the patient's skin to draw blood into the capillary sample tube 52. The capillary sample tube 52 draws the sample fluid into the patient identification sensor 50 to a reaction chamber 56 which includes a reagent 58. In another embodiment, the reaction chamber 56 may be positioned at the edge of the identification sensor 50 and the wireless sensor 16, eliminating the capillary sample tube. In such an embodiment, placement of the wireless sensor 16 on the patient places the reaction chamber 56 in contact with the patient's skin. Such an embodiment may be used to sample skin or perspiration directly into the reaction chamber 56.

In an exemplary embodiment, the reagent 58 reacts with the sample fluid. A transducer 60 positioned at the reaction chamber 56 senses the result of the reaction between the reagent 58 and the sample fluid. The transducer 60 provides identification data in the form of a signal to the processor 40. The processor 40 uses the identification data to create an identifier that is appended to the physiological data transmitted by the wireless sensor 16. In an exemplary embodiment the identifier is a numerical value that represents the identification data. A signal representative of the identifier may be transmitted by the wireless sensor.

In exemplary embodiments, the patient identification sensor is a single-use sensor that performs the above analysis when the sensor is first secured to the patient. Since the unique quality or characteristic of the patient is specific to the patient, the quality or characteristic stays the same for the duration that the wireless sensor is secured to the patient and therefore does not need to be detected again after the initial registration and set up of the wireless sensor. Once the wireless sensor has determined the identification data and the identifier to be appended to the physiological data based upon the identification data, the processor continues to transmit with the determined identifier. This is particularly true if the wireless sensor is a disposable wireless sensor, only being secured to a patient once and used until it is removed and/or replaced by a clinician.

Figure 4:
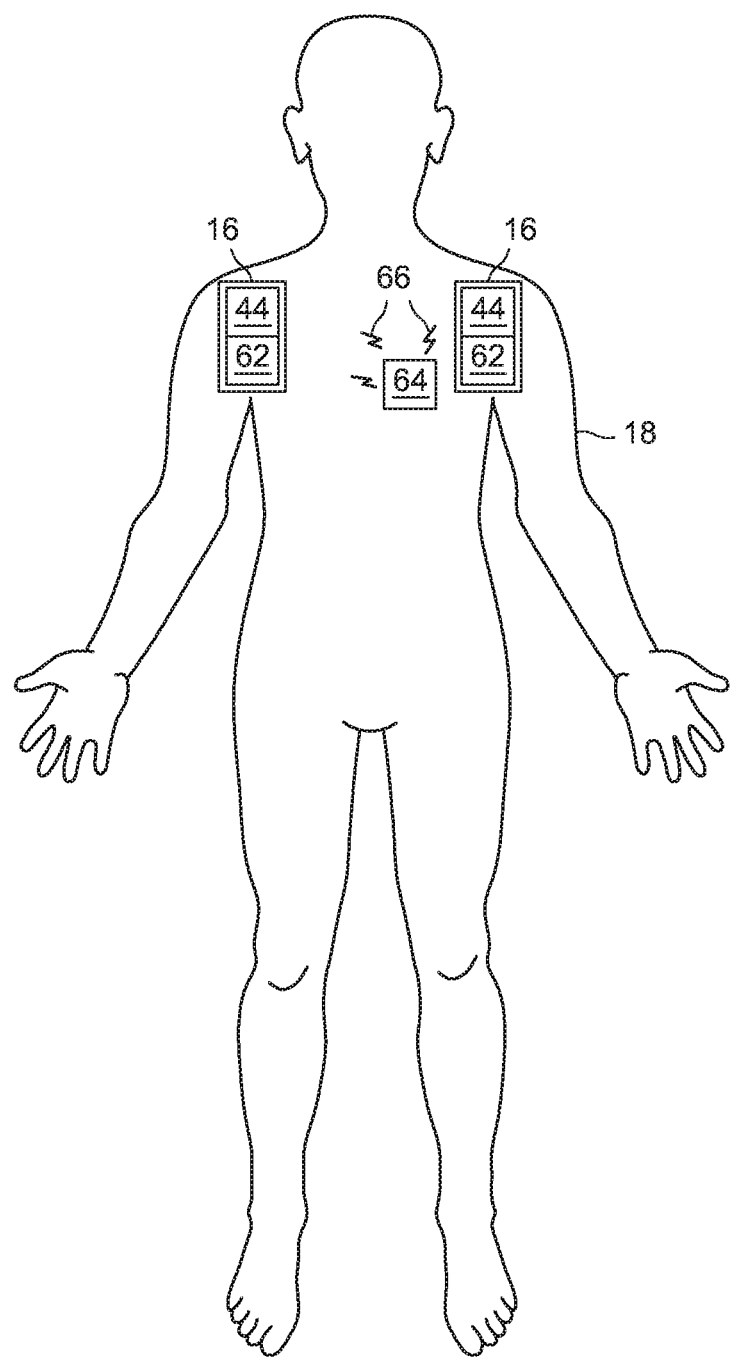
FIG. 4 depicts an additional exemplary embodiment of a patient identification sensor.

FIG. 4 depicts an exemplary embodiment of wireless sensors 16 that include another exemplary embodiment of patient identification sensors 62 in which the patient identification sensors 62 determine identification data from an implanted device 64. As described with respect to previous embodiments, the wireless sensors 16 use the determined identification data to modify the physiological data transmitted from a transmitter 44 of the wireless sensors 16. In FIG. 4, the implanted device 64 is an electronic medical device previously implanted in the patient 18. The implanted device 64 may exemplarily be a therapeutic, diagnostic, and/or identifying medial device, but in general is a device that already exists within the patient, having previously been implanted within the patient. In non-limiting embodiments, the secondary implanted device may exemplarily be a pacemaker, an insulin pump, or an identification device.

In exemplary embodiments, the implanted device 64 outputs a potential 66 or other electrical signal that is carried throughout the patient's body. This potential 66 embodies in it a unique identifying signal or value. In such exemplary embodiments, the patient identification sensor 62 may exemplarily be potential sensor or electrode and the wireless sensor 16 senses the potential and determines identification data therefrom. In another embodiment, the implanted device emits wireless identification signal, in an exemplary embodiment, the wireless identification signal is a radio frequency identification (RFID) signal. In such an embodiment, the patient identification sensor is an RFID reader or another antenna configured to receive the RFID signal emitted from the secondary implanted device at a short distance. The RFID signal may encode within it a unique identifier associated with the patient, and the wireless sensor determines this unique identifier as the identification data. In other exemplary embodiments, the wireless identification signal is an ultrasonic communication or another form of RF communication.

Thus, as depicted in FIG. 4, each of the wireless sensors 16 secured to the patient 18 is configured to sense the same patient identification data, for example a signal emitted from the secondary implanted device 64. Because all of the wireless sensors 16 are sensing the same patient identification data, all of the wireless sensors 16 will determine the same patient identification data. This results in each of the wireless sensors determining the same identifier that is appended to the physiological data transmitted from each of the wireless sensors 16 secured to the patient 18.

Citations to references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A sensor comprising:
   a physiological sensor configured to obtain physiological data from a patient;
   an identification sensor configured to detect an electrical potential from the patient as identification data;
   a processor that receives the physiological data and the identification data, the processor produces a unique identifier from the identification data, the processor appends the unique identifier to the physiological data; and
   a communication system operable by the processor to wirelessly transmit the combined physiological data and unique identifier.

2. The sensor of claim 1, wherein the identification data is an electrical signal of an implantable device inside the patient.

3. The sensor of claim 2, wherein the implantable device is a pacemaker.

4. The sensor of claim 1, wherein as the identification data is a biopotential.

5. The sensor of claim 1, wherein the physiological sensor and the identification sensor are embodied in a single biopotential sensor.

6. A wireless sensing system comprising:
   a first wireless sensor comprising a physiological sensor configured to obtain first physiological data from a first patient, an identification sensor configured to detect an electrical potential from the first patient to obtain first identification data, wherein the first identification data is electrical potential data, a processor that receives the first physiological data and the first identification data, produces a first unique identifier from the first identification data, appends the first unique identifier to the first physiological data, and operates a communication system to wirelessly transmit the combined first physiological data and first unique identifier;
   a second wireless sensor comprising a physiological sensor configured to obtain second physiological data from a second patient, an identification sensor configured to detect an electrical potential from the second patient to obtain second identification data, wherein the second identification data is electrical potential data, a processor that receives the second physiological data and the second identification data, produces a second unique identifier from the second identification data, appends the second unique identifier to the second physiological data, and operates a communication system to wirelessly transmit the combined second physiological data and second unique identifier;
   a communication system defining a communication area within which the communication system defining the communication area will receive transmissions from wireless sensors within the communication area; and
   a processor communicatively connected to the communication system, wherein the processor concurrently receives the combined first physiological data and first unique identifier from the first wireless sensor and the combined second physiological data and second unique identifier from the second wireless sensor and the processor sorts the first physiological data from the second physiological data based upon the first and second unique identifiers then stores the first physiological data associated with the first patient based upon the first unique identifier, and stores the second physiological data associated with the second patient based upon the second unique identifier.

7. The wireless sensing system of claim 6, wherein the communication system further receives a plurality of transmissions each comprising physiological data combined with a unique identifier, and the processor compares the unique identifiers of the received plurality of transmissions to the first unique identifier and the second unique identifier and stores the physiological data of the received plurality of transmissions with the first physiological data or the second physiological data based upon this comparison.

8. The wireless sensing system of claim 6, further comprising:
   a first implanted device that produces a first signal within the first patient and a second implanted device that produces a second signal within the second patient; and
   wherein the identification sensors of the first and second wireless sensors respectively obtain the first signal and the second signal and the processors of the first and second wireless sensors respectively produce first and second unique identifiers based upon the received first and second signals.

9. The wireless sensing system of claim 8, wherein the first and second signals are at least one of electrical potentials and radio frequency (RF) signals.

10. The wireless sensing system of claim 8, wherein the first and second implanted devices are selected from a pacemaker, an insulin pump, and an identification tag.

11. The wireless sensing system of claim 6, wherein the processor registers the first unique identifier to the first patient and the second unique identifier to the second patient and as the processor receives transmissions of combined physiological data and unique identifiers through a hub, the processor sorts the physiological data based upon the first unique identifier and the second unique identifier and further comprising:
   a first plurality of wireless sensors, the first plurality of wireless sensors comprising the first wireless sensor, each wireless sensor of the first plurality of wireless sensors transmits the combined physiological data and the first unique identifier as obtained by each wireless sensor of the first plurality of wireless sensors; and
   a second plurality of wireless sensors, the second plurality of wireless sensors comprising the second wireless sensor, each wireless sensor of the second plurality of wireless sensors transmits the combined physiological data and the second unique identifier as obtained by each wireless sensor of the first plurality of wireless sensors;
   wherein the processor associates the physiological data transmitted with the first unique identifier to the first patient and associates the physiological data transmitted with the second unique identifier to the second patient.

12. A method of wireless sensing, the method comprising:
   placing a first plurality of wireless sensors on a first patient;
   each wireless sensor of the first plurality of wireless sensors individually producing the same first unique identifier based upon a characteristic of the first patient;

each wireless sensor of the first plurality of wireless sensors obtaining physiological data from the first patient;
each wireless sensor of the first plurality of wireless sensors transmitting the obtained physiological data and the first unique identifier from that wireless sensor;
receiving the physiological data and the first unique identifier from the first plurality of wireless sensors at a processor; and
after receiving the physiological data and the first unique identifier from the first plurality of wireless sensors at the processor, associating the received physiological data to the first patient with the processor based upon the received first unique identifier.

13. The method of claim 12, further comprising:
placing a second plurality of wireless sensors on a second patient;
each wireless sensor of the second plurality of wireless sensors individually producing the same second unique identifier based upon a characteristic of the second patient;
each wireless sensor of the second plurality of wireless sensors obtaining physiological data from the second patient;
each wireless sensor of the second plurality of wireless sensors transmitting the obtained physiological data and the second unique identifier from that wireless sensor;
receiving the physiological data and the second unique identifier from the second plurality of wireless sensors at the processor; and
after receiving the physiological data and the second unique identifier from the second plurality of wireless sensors at the processor, sorting the received physiological data based upon the first and second unique identifiers received along with the physiological data;
then associating the received physiological data to the first patient or the second patient with the processor based upon the received first and second unique identifiers.

14. The method of claim 13, further comprising:
registering the first unique identifier to a patient record of the first patient; and
registering the second unique identifier to a patient record of the second patient.

15. The method of claim 14, wherein registration occurs retrospectively after the physiological data and the first and second unique identifiers are received by the processor.

16. The method of claim 12, further comprising:
transmitting an identifying signal from an implanted device implanted within the first patient; and
receiving the identifying signal through the first patient at each of the first plurality of wireless sensors;
wherein the identifying signal is the characteristic of the first patient.

17. A wireless sensing system comprising:
a first wireless sensor comprising a physiological sensor configured to obtain first physiological data from a first patient, a first identification sensor configured to detect a unique characteristic of the first patient to obtain first identification data, the first identification data being an electrical potential acquired from the first patient by the identification sensor, a first sensor processor that receives the first physiological data and the first identification data and operates a communication system to wirelessly transmit the first physiological data and the first identification data;
a second wireless sensor comprising a physiological sensor configured to obtain second physiological data from a second patient, a second identification sensor configured to detect a unique characteristic of the second patient to obtain second identification data the second identification data being an electrical potential acquired from the second patient by the second identification sensor, a second sensor processor that receives the second physiological data and the second identification data and operates a communication system to wirelessly transmit the second physiological data and the second identification data;
a communication system defining a communication area within which the communication system defining the communication area will receive transmissions from wireless sensors within the communication area; and
a processor communicatively connected to the communication system, wherein the processor concurrently receives the first physiological data, the first identification data, second physiological data, second identification data from the communication system, produces a first unique identifier from the first identification data and produces a second unique identifier from the second identification data, and stores the first physiological data in association with the first unique identifier and stores the second physiological data in association with the second unique identifier.

18. The wireless sensing system of claim 17 further comprising:
a first plurality of wireless sensors comprising the first wireless sensor, each wireless sensor of the first plurality obtains first identification data that results in the same first unique identifier when processed by the processor; and
a second plurality of wireless sensors comprising the second wireless sensor, each wireless sensor of the second plurality of wireless sensors obtains second identification data that results in the same second unique identifier when processed by the processor.

19. The wireless sensing system of claim 18, wherein the processor sorts physiological data received from the first plurality of wireless sensors from physiological data received from the second plurality of wireless sensors based upon the first unique identifier and the second unique identifier and stores the first physiological data associated with the first patient based upon the first unique identifier and stores the second physiological data associated with the second patient based upon the second unique identifier.

20. The wireless sensing system of claim 17, wherein the first wireless sensor and the second wireless sensor are located within the communication area and the communication system receives the first physiological data, the first identification data, the second physiological data, and the second identification data.

* * * * *